United States Patent [19]

Le Baut et al.

[11] Patent Number: 5,290,797
[45] Date of Patent: Mar. 1, 1994

[54] BENZOPYRAN COMPOUNDS

[75] Inventors: Guillaume Le Baut, Saint Sebastien sur Loire; Jean-Paul Babingui; Jean-Michel Robert, both of Nantes; Pierre Renard, Versailles; Jean-Francois Renaud de la Faverie, Le Chesnay; Gérard Adam, Le Mesnil le Roi, all of France

[73] Assignee: Adir et Compagnie, Courbevoie, France

[21] Appl. No.: 846,218

[22] Filed: Mar. 4, 1992

[30] Foreign Application Priority Data

Mar. 8, 1991 [FR] France .................. 91 02799

[51] Int. Cl.$^5$ ............... C07D 405/12; A61K 31/44
[52] U.S. Cl. ................................. 514/337; 546/269
[58] Field of Search .................. 546/269; 514/337

[56] References Cited

U.S. PATENT DOCUMENTS 5,017,604 5/1991 Belliotti et al. .................. 560/18

FOREIGN PATENT DOCUMENTS

PCT/US88/-
01212 4/1988 PCT Int'l Appl. .
88/08424 11/1988 PCT Int'l Appl. .

OTHER PUBLICATIONS

Davies, Kelvin J. A., "Oxidative Damage and Repair, Chemical, Biological and Medical Aspects", Pergamon Press, p. xxi, 1990.
Halliwell, Barry, "Drug Antioxidant Effects-A Basis for Drug Selection", USA in Drugs 42(4), 569-605 (1991).
Slater, T., and Jacob, H. S., "New Developments In Free Radical Research", International Conference held Oct. 15-16, 1990.
Goodman and Gilman, "The Pharmacological Basis of Therapeutics", 8th Edition, Pergamon Press, p. 603 1990.
Floyd, R. A., "Role of Oxygen-Free Radicals In Carcinogenesis and Brain Ischemia", The FASEB Journal 4, pp. 2587-2597 (1990).

Primary Examiner—Jane T. Fan
Attorney, Agent, or Firm—Gordon W. Hueschen

[57] ABSTRACT

A compound selected from those of the formula I:

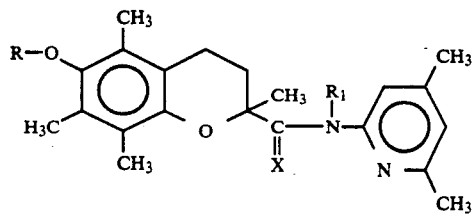

in which:
$R_1$ represents hydrogen or alkyl having 1 to 3 inclusive carbon atoms,
R represents hydrogen, alkyl having 1 to 4 inclusive carbon atoms, or acyl —CO—R' in which R' represents alkyl having 1 to 4 inclusive carbon atoms,
X represents O or $H_2$,
an isomer,
and an addition salt thereof with a pharmaceutically-acceptable acid or base, and
medicinal products containing the same which are useful in treating or in preventing disorder resulting from or associated with phenomena of peroxidation and disturbance of the synthesis of eicosanoids.

9 Claims, No Drawings

BENZOPYRAN COMPOUNDS

The present invention relates to new benzopyran compounds.

Numerous benzopyran compounds are known, especially the tocopherols, vitamin E compounds exhibiting in particular antioxidant properties. Numerous tocopherol compounds have been prepared by modification of the side chain of alkanoic nature, without an increase in the antioxidant activity. Other benzopyran compounds, such as (6-hydroxy-2,5,7,8-tetramethylchroman-2-yl)-carboxylic acid have a good antioxidant activity, but have been used in industry only and not for therapeutic purposes.

More recently, Patent Application WO 88/08424 has described other chroman-2-yl carboxylic acid compounds and, more generally, (chroman-2-yl)alkylcarboxylic acid compounds, having valuable antioxidant properties.

The Applicant has now discovered new benzopyran compounds and, more particularly, (benzopyran-2-yl)carboxylic or (chroman-2-yl)carboxylic acid compounds having an antioxidant activity distinctly superior to those of the WO 88/08424 Application which constitutes the closest prior art.

More specifically, the invention relates to new benzopyran compounds corresponding to the general formula I

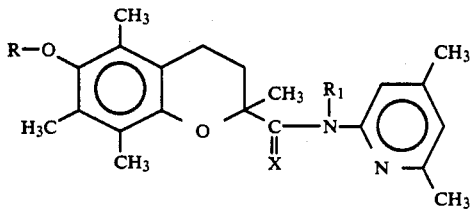

in which:
$R_1$ represents a hydrogen atom or an alkyl radical containing from 1 to 3 carbon atoms,
R represents a hydrogen atom, an alkyl radical containing from 1 to 4 carbon atoms, or an acyl radical —CO—R' in which R' represents an alkyl radical containing from 1 to 4 carbon atoms,
X represents O or $H_2$,
their isomers,
and also, when X represents $H_2$, their addition salts with a pharmaceutically acceptable acid and, when R represents a hydrogen atom, their addition salts with a pharmaceutically acceptable base.

Of the pharmaceutically acceptable acids or bases that may be used to convert the compounds of the invention into salts there may be mentioned, by way of non-limiting example, hydrochloric, hydrobromic, sulphuric, nitric, oxalic, malic, maleic, succinic, tartaric, methanesulphonic, camphoric and camphosulphonic acid, sodium hydroxide, potassium hydroxide, triethylamine, diethylamine, ethanolamine, arginine, lysine, and diethanolamine.

A way for obtaining compounds of formula I may be a process wherein (6-hydroxy-2,5,7,8-tetramethylchroman-2-yl)carboxylic acid is esterified in a basic anhydrous medium by an acid anhydride of the formula R'—CO—O—CO—R', or an acid halide of the formula R'—CO—Hal, in which formulae R' has the same meaning as in formula I and Hal represents a halogen atom, to obtain an acid of formula II

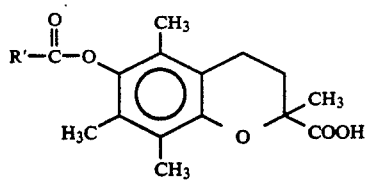

in which R' has the same meaning as in formula I, which is converted into its chloride by the action of thionyl chloride in anhydrous medium and then treated, in a suitable solvent in the presence of an alkaline agent, with an amine of formula III

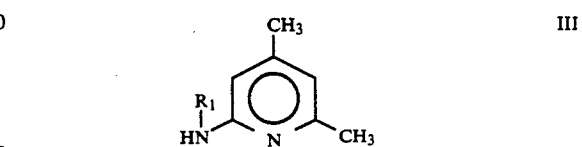

in which $R_1$ has the same meaning as in formula I, to obtain a compound of formula $I_a$

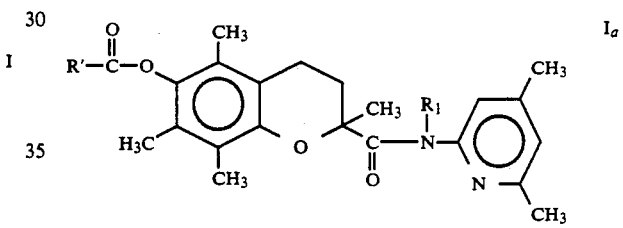

in which R' and $R_1$ are as defined hereinbefore, a particular instance of compounds of formula I in which R represents —CO—R' and X represents an oxygen atom, which is then hydrolysed by the action of an alkali metal or alkaline earth metal hydroxide to form a compound of formula $I_b$

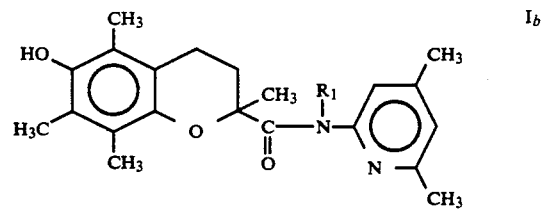

in which $R_1$ is as defined hereinbefore, a particular instance of compounds of formula I in which R represents a hydrogen atom and X represents an oxygen atom, which may then be:
- converted into an addition salt with a pharmaceutically acceptable base,
- or etherified with a halogenated compound of formula $R_2$Hal in which $R_2$ represents an alkyl radical having from 1 to 4 carbon atoms and Hal represents a halogen atom, to obtain a compound of formula $I_c$

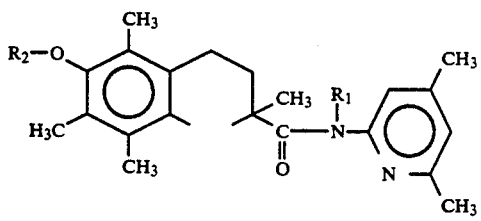

in which $R_1$ and $R_2$ are as defined hereinbefore, a particular instance of compounds of formula I an which X represents an oxygen atom and R represents a group $R_2$ as defined hereinbefore,

- or reduced by the action of an alkali metal mixed hydride to form a compound of formula $I_d$

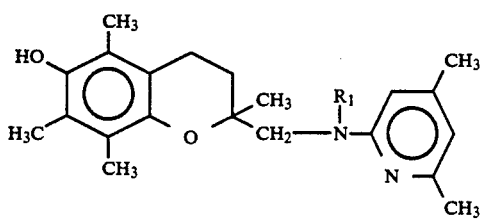

in which $R_1$ is as defined hereinbefore, a particular instance of compounds of formula I in which R represents a hydrogen atom and X represents $H_2$, which may either be

- converted into a salt by the action of a pharmaceutically acceptable base or acid, or
- etherified or esterified by the action of a compound of formula $R'_2$-Hal in which Hal represents a halogen atom and $R'_2$ represents and alkyl radical having from 1 to 4 carbon atoms or an acyl radical —CO—R' as defined in formula I, to form a compound of formula $I_e$

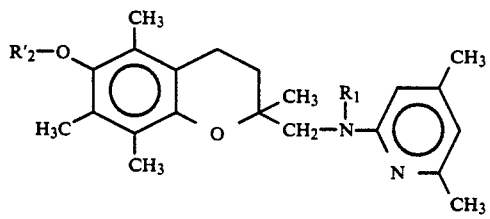

in which R and $R'_2$ are as defined hereinbefore, a particular instance of compounds of formula I in which X represents $H_2$ and R has the meanings of $R'_2$, which, if desired, is converted into a salt by the action of a pharmaceutically acceptable acid.

The compounds of formulae $I_a$, $I_b$, $I_c$, $I_d$, and $I_e$ form the totality of the compounds of formula I, which may, if desired, be separated into their isomers in accordance with conventional methods.

Compared with compounds of the prior art, the compounds of the present invention surprisingly exhibit very substantial antioxidant properties. Pharmacological studies have in particular demonstrated that those compounds have remarkable protective activities within the framework of cellular lipid and low-density lipoprotein (LDL) peroxidation processes.

These activities are 100 times greater than that of the closest compound of the prior art, that is to say Example 102 of formula (a) of the WO 88/08424 Application:

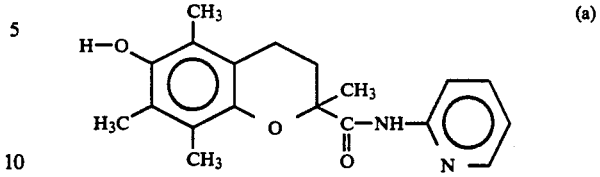

Furthermore, the compounds of the present invention have a powerful inhibiting effect upon eicosanoid biosynthesis, of which several stages go through peroxide compounds which are potent generator of free radicals, an effect not exhibited by the closest prior art compound. The compounds of the invention, which have both lipid peroxidation-inhibiting and eicosanoid biosynthesis-inhibiting properties, may therefore be expected to have an especially new and beneficial effect in the case of disorders involving not only peroxidation of membrane lipids but also a disturbance in the synthesis of eicosanoids.

The compounds of the present invention may thus be used in the treatment or prevention of disorders resulting from or associated with such phenomena of peroxidation and disturbances of eicosanoid synthesis and especially central or peripheral ischaemic disorders, inflammatory diseases such as rheumatoid arthritis, metabolic disorders such as atheroma and arteriosclerosis, respiratory disorders such as asthma or emphysema, disorders of immunological origin such as lupus erythematosus, allergic reactions, certain cancers, cerebral or cutaneous ageing, and also the prevention and treatment of damage resulting from surgical traumas, such as organ reperfusion.

The present invention also relates to pharmaceutical compositions comprising a compound of formula I, or an addition salt thereof with a pharmaceutically acceptable acid or base, alone or in combination with one or more inert non-toxic excipients.

Among the pharmaceutical compositions of the invention there may be mentioned more especially those that are suitable for oral, parenteral, nasal, rectal, perlingual, ocular or pulmonary administration, and especially injectable preparations, aerosols, eye or nose drops, tablets, film-coated tablets or dragées, soft gelatin capsules, hard gelatin capsules, creams, ointments, and dermal gels.

The dosage varies in accordance with the age and weight of the patient, the administration route, the nature of the disorder and of possibly associated treatments, and ranges from 0.5 mg to 2 grams per 24 hours.

The Examples which follow illustrate the invention but do not limit it in any way.

The starting material is described in the literature.

Example 1:
N-(4,6-dimethylpyridin-2-yl)-(6-acetoxy-2,5,7,8-tetramethylchroman-2-yl)carboxamide STEP A: (6-acetoxy-2,5,7,8-tetramethylchroman-2-yl)carboxylic acid Dissolve 50 grams (0.2 mol) of (6-hydroxy-2,5,7,8-tetramethylchroman-2-yl)carboxylic acid in 150 cm³ of anhydrous pyridine. Add dropwise 9.4 cm³ (0.1 mol) of acetic anhydride under a stream of nitrogen. Stir for 2 hours at a temperature of 30° C. After cooling, pour the mixture onto some ice, extract the resulting product with diethyl ether, and wash the organic phase with a 0.2N hydrochloric acid solution, and then with water until neutral. After evaporation of the solvent, an oily mass is collected which crystallises after trituration in diisopropyl ether.

STEP B: N-(4,6-dimethylpyridin-2-yl)-(6-acetoxy-2,5,7,8-tetramethylchroman-2-yl)carboxamide Dissolve 5.4 grams (18.47 mmol) of the compound obtained in Step A in 30 cm³ of anhydrous benzene, add 2 cm³ (27.41 mmol) of thionyl chloride, heat under reflux for 3 hours, and evaporate the solvent in vacuo, at the same time eliminating excess thionyl chloride. Dissolve the resulting acid chloride in 30 cm³ of dichloroethane.

In another vessel, dissolve 2.26 grams (18.5 mmol) of 2-amino-4,6-dimethylpyridine in 20 cm³ of dichloroethane, add 7.7 cm³ of triethylamine and add dropwise to that mixture the acid chloride solution obtained above. After stirring for 8 hours, evaporate the solvent in vacuo, take up the residue in 30 cm³ of water, neutralise with an NaHCO₃ solution, extract with methylene chloride, wash the organic phase with water and then dry it over sodium sulphate. After evaporation of the solvent, purify by chromatography on a column of silica gel using methylene chloride as eluant.

The desired product is obtained (yield 71%)
- Melting point: 128°–129° C.
- IR spectrum characteristics:
    vNH: 3410, 3390 cm⁻¹
    vCO ester: 1760 cm⁻¹
    vCO amide 1690 cm⁻¹

Example 2 N
(4,6-dimethylpyridin-2-yl)-(6-hydroxy-2,5,7,8-tetramethylchroman 2-yl)carboxamide Dissolve 5.25 grams (13.24 mmol) of the compound of Example 1 in 80 cm³ of ethanol, add 40 cm³ of water, then 3.18 grams of sodium hydroxide dissolved in 10 cm³ of water and 10 cm³ of ethanol. Stir under nitrogen for 3 hours, dilute the mixture with water acidified with acetic acid, filter, wash with water and then with ether, dry and evaporate. 4.49 grams of the compound of the Example (yield 96%) are obtained.
- Melting point: 244°–245° C.
- IR spectrum characteristics:
    vNH: 3380 cm⁻¹
    vC—H: 2990, 2980, 2930 cm⁻¹
    vC=O: 1700 cm⁻¹

Example 3: N-(4,6-dimethylpyridin 2 yl)-(6-methoxy-2,5,7,8-tetramethylchroman 2 yl)carboxamide At a temperature of 0° C., add 0.25 grams (6.25 mmol) of 60% sodium hydride to a suspension of 2.2 grams (6.2 mmol) of the compound of Example 2 in 40 cm³ of dimethylformamide. Stir for one hour and then pour in 0.4 cm³ (6.42 mmol) of methyl iodide dissolved in 5 cm³ of dimethylformamide and continue stirring for 90 minutes. Pour the solution onto some ice, acidify with acetic acid, extract with methylene chloride, wash the organic phase with water, dry over sodium sulphate, evaporate the solvent, and purify the resulting oily residue by chromatography on silica gel using methylene chloride as eluant.

1.62 grams of the compound of the Example (yield 70.8%) are obtained.
- Melting point: 97°–98° C.
- IR spectrum characteristics:
    vNH: 3400, 3360 cm⁻¹
    vCH: 2980, 2920 cm⁻¹
    vCO: 1680 cm⁻¹
    vNH: 1520 cm⁻¹

Examples 4 to 6

By replacing the 2-amino-4,6-dimethylpyridine in Step B of Example 1 with N-(4,6-dimethylpyridin-2-yl)ethylamine and then proceeding as in Examples 2 and 3, the following are obtained in succession:

Example 4:
N-ethyl-N-(4,6-dimethylpyridin-2-yl)-(6-acetoxy-2,5,7,8-tetramethylchroman-2-yl)carboxamide Yield: 84%
- Melting point: 95°–96° C.
- IR spectrum characteristics:
    vCH₂, CH₃: 2980, 2920 cm⁻¹
    vCO ester: 1750 cm⁻¹
    vCO amide: 1645 cm⁻¹

Example 5:
N-ethyl-N-(4,6-dimethylpyridin-2-yl)-(6-hydroxy-2,5,7,8-tetramethylchroman-2-yl)carboxamide Yield 86%
- Melting point: 170°–171° C.
- IR spectrum characteristics:
    vOH: 3500, 3200 cm⁻¹
    vCH₂, CH₃: 2980, 2920, 2860 cm⁻¹
    vCO: 1620 cm⁻¹

Example 6:
N-ethyl-N-(4,6-dimethylpyridin-2-yl)-(6-methoxy-2,5,7,8-tetramethylchroman-2-yl)carboxamide Yield 67.5%
- Melting point: 90°–92° C.
- IR spectrum characteristics:
    vCH₃: 2970, 2920 cm⁻¹
    vCO: 1640 cm⁻¹

Examples 7 to 9

By replacing the 2-amino-4,6-dimethylpyridine in Step B of Example 1 with N-(4,6-dimethylpyridin-2-yl)methylamine and then proceeding as in Examples 2 and 3, the following are obtained in succession:

Example 7:
N-methyl-N-(4,6-dimethylpyridin-2-yl)-(6-acetoxy-2,5,7,8-tetramethylchroman-2-yl)carboxamide Yield: 74%
- Melting point: 133°–134° C.

Example 8:
N-methyl-N-(4,6-dimethylpyridin-2-yl)-(6-hydroxy-2,5,7,8-tetramethylchroman-2-yl)carboxamide Yield: 87%
- Melting point: 141°–142° C.

Example 9: N-methyl-N-(4,6-dimethylpyridin-2 yl)-(6-methoxy-2,5,7,8-tetramethylchroman-2-yl)carboxamide Yield: 84%
- Melting point: 135°–136° C.

Examples 10 to 12:

By replacing the methyl iodide in Examples 3, 6, and 9 with 1-bromopropane there are obtained respectively, in the same manner:

Example 10: N-(4,6-dimethylpyridin-2-yl)-(6-propoxy 2,5,7,8-tetramethylchroman-2-yl)carboxamide Yield: 77%
- IR spectrum characteristics:
  vCH$_2$, CH$_3$: 2970, 2920, 2870 cm$^{-1}$
  vCO: 1670 cm$^{-1}$

Example 11: N-ethyl-N-(4,6-dimethylpyridin-2-yl)-(6-propoxy-2,5,7,8-tetramethylchroman-2-yl)carboxamide Yield: 69%
- IR spectrum characteristics:
  vCH$_2$, CH$_3$: 2970, 2910, 2880 cm$^{-1}$
  vCO: 1660 cm$^{-1}$

Example 12: N-methyl-N-(4,6-dimethylpyridin-2-yl)-(6-propoxy-2,5,7,8-tetramethylchroman-2-yl)carboxamide Yield 72%
- IR spectrum characteristics:
  vCH$_2$, CH$_3$: 2980, 2920, 2870 cm$^{-1}$
  vCO: 1670 cm$^{-1}$
  vC=C, C=N: 1620, 1560 cm$^{-1}$

Examples 13 to 15:

By replacing the acetic anhydride in Step A of Example 1 with trimethylacetic acid chloride and then proceeding as in Examples 1, 4, and 7, in Step B, there are obtained, respectively:

Example 13: N-(4,6-dimethylpyridin-2-yl)-(6-trimethylacetoxy-2,5,7,8-tetramethylchroman-2-yl)carboxamide

- IR spectrum characteristics:
  vNH: 3410 cm$^{-1}$
  vCH, CH$_3$: 2970, 2920, 2860 cm$^{-1}$
  vCO ester = 1750 cm$^{-1}$
  vCO amide = 1690 cm$^{-1}$

Example 14: N-ethyl-N-(4,6-dimethylpyridin-2-yl)-(6-trimethylacetoxy-2,5,7,8-tetramethylchroman-2-yl)carboxamide

- IR spectrum characteristics:
  vCH, CH$_2$, CH$_3$: 2970, 2910, 2850 cm$^{-1}$
  vCO ester = 1740 cm$^{-1}$
  vCO amide = 1695 cm$^{-1}$

Example 15: N-methyl-N-(4,6-dimethylpyridin-2-yl)-(6-trimethylacetoxy-2,5,7,8 tetramethylchroman-2-yl)carboxamide

- IR spectrum characteristics:
  vCH, CH$_3$: 2970, 2915, 2860 cm$^{-1}$
  vCO ester = 1750 cm$^{-1}$
  vCO amide = 1695 cm$^{-1}$

Example 16: N-(4,6 dimethylpyridin-2-yl)-(6-hydroxy-2,5,7,8-tetramethylchroman-2-yl)methylamine Dissolve 2.2 grams (6.2 mmol) of the compound of Example 2 in 120 cm$^3$ of anhydrous tetrahydrofuran, add 0.94 grams of lithium aluminium hydride, and heat under reflux for 3 hours.

After cooling, pour the mixture onto some ice, o filter and extract the product with warm chloroform. Dry the organic phase over sodium sulphate. After evaporation of the solvent, triturate the resulting oily residue with diisopropyl ether. 1.7 grams of the product of the Example are obtained:

- Melting point: 184°–185° C.
- IR spectrum characteristics:
  vNH: 3380 cm$^{-1}$
  vCH$_2$, CH$_3$: 2970, 2920 cm$^{-1}$

Example 17: N-(4,6-dimethylpyridin-2-yl)-(6-methoxy-2,5,7,8-tetramethylchroman-2-yl)methylamine By replacing the compound of Example 2 in Example 16 with the compound of Example 3, the compound of Example 17 is obtained in the same manner:
Yield: 86%
Melting point: 207°–208° C.

Example 18: N-(4,6-dimethylpyridin-2-yl)-(6-acetoxy-2,5,7,8-tetramethylchroman-2 yl)methylamine, maleate By proceeding as in Example 1, Step A, but replacing the (6-hydroxy-2,5,7,8-tetramethylchroman-2-yl)carboxylic acid with the compound of Example 16, and after conversion into a salt using maleic acid, there is obtained the compound of Example 18, which is recrystallised from ethyl acetate.
Yield 62%
Melting point: 157°–158° C.

Examples 19 to 21

By replacing the compound of Example 2 in Example 16 with the compound of Example 5, and proceeding as in Examples 16, 17, and 18, there are obtained respectively, in the same manner:

Example 19: N-ethyl-N-(4,6-dimethylpyridin-2-yl)-(6-hydroxy-2,5,7,8 tetramethylchroman-2-yl)methylamine Example 20: N-ethyl-N-(4,6-dimethylpyridin-2-yl)-(6-methoxy-2,5,7,8-tetramethylchroman-2 yl)methylamine Example 21: N-ethyl-N-(4,6-dimethylpyridin-2-yl)-(6-acetoxy-2,5,7,8-tetramethylchroman-2-yl)methylamine

PHARMACOLOGICAL STUDY OF THE COMPOUNDS OF THE INVENTION

The compounds are compared with the closest prior art compound, which is Example 102 of formula (a) of the WO 88/08424 application:

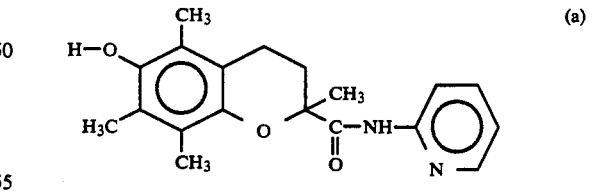

Example 22: STUDY OF THE ANTIPEROXIDANT ACTIVITY

The action of the compounds of the invention, capable of capturing .OH radicals, on the one hand on the spontaneous peroxidation of lipids and, on the other hand, on the peroxidation induced by the $Fe^{2+}$ ascorbate system (10 µM–250 µM), was studied in rat brain homogenates.

For the measurement of the spontaneous lipid peroxidation, the rat brain homogenates are placed in the presence or absence of the compounds to be tested for a period of 60 minutes at 37° C. The reaction is stopped at 0° C. and the amount of malonic dialdehyde is calculated with the aid of thiobarbituric acid by the method according to YAGI, K (1976) Biochem. Med., 15, 212-216. The lipid peroxidation is determined by the substances reacting with the thiobarbituric acid expressed in nanomols of malonic dialdehyde.

For the measurement of the induced lipid peroxidation, the methodology is identical to that above except for the addition to the homogenate of the radical-inducing system $Fe^{2+}$ ascorbate. The reference substances are probucol and vitamin E.

The concentrations of the test compounds that inhibit peroxidation of the substrate by 50% are calculated.

It is apparent that the compounds of the invention have a particularly intense antiperoxidant activity since it is superior by a factor of 100 to that of the closest prior art compound. This very interesting result occurs whether the peroxidation is spontaneous or is induced by a chemical system.

Example 23: STUDY OF THE PROPERTY OF PROTECTION AGAINST LDL OXIDATION

The capacity of the compounds of the invention to reduce the proportions of oxidised LDLs was measured in the following manner. Native LDLs, a $Cu^{2+}$ system that generates free radicals and the compounds to be tested are incubated together for 24 hours.

The results are obtained after analysing the mixture by a high-performance chromatography technique: FPLC (Fast Protein Liquid Chromatography). The protective capacity of the compound tested is determined after comparing the resulting chromatogram with that of the positive reference control which is probucol.

It appears clearly that the compounds of the invention have a very substantial protective capacity that is significantly superior to that of the closest prior art compound.

By way of comparison, at a concentration of $10^{-5}M$, the level of protection obtained with the compounds of the invention exceeds that of probucol and is more than 5 times greater than that of the closest prior art compound.

Example 24: STUDY OF THE EICOSANOID BIOSYNTHESIS-INHIBITING ACTIVITY OF THE COMPOUNDS A study of the eicosanoid biosynthesis-inhibiting activity of the compounds was carried out using human platelets activated beforehand with thrombin and placed in the presence of the products to be tested.

The production of thromboxane $B_2$, which is a major product of eicosanoid biosynthesis in platelets, is determined by radioimmunological assay (RIA).

The compounds of the invention inhibit very significantly the production of thromboxane $B_2$, whilst the closest prior art compound has no effect on that production. By way of example, at a concentration of $10^{-5}M$, the compounds of the invention cause an inhibition of the production of thromboxane $B_2$ of the order of 80%.

Example 25: PHARMACEUTICAL COMPOSITION: TABLETS

Tablets each containing 50 mg of N-(4,6-dimethylpyridin-2-yl)-(6-hydroxy-2,5,7,8-tetramethylchroman-2-yl)carboxamide.

Preparation formula for 1000 tablets: N-(4,6-dimethylpyridin-2-yl)-(6-hydroxy-2,5,7,8-tetramethylchroman-2-yl)

| | |
|---|---|
| carboxamide | 50 g |
| wheat starch | 15 g |
| cornstarch | 15 g |
| lactose | 65 g |
| magnesium stearate | 2 g |
| silica | 1 g |
| hydroxypropylcellulose | 2 g |

I claim:

1. A compound selected from the group consisting of those of the formula I

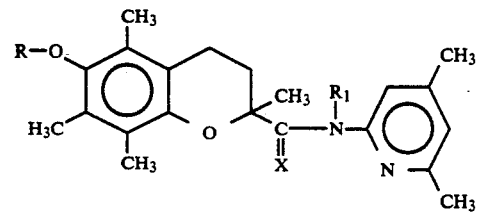

in which:
$R_1$ represents hydrogen or alkyl having 1 to 3 inclusive carbon atoms,
R represents hydrogen, alkyl having 1 to 4 inclusive carbon atoms, or acyl —CO—R' in which R' represents alkyl having 1 to 4 inclusive carbon atoms,
X represents O, an isomer thereof, and, when R represents hydrogen, an addition salt thereof with a pharmaceutically-acceptable base.

2. A compound according to claim 1 selected from those in which R represents hydrogen, an isomer thereof, and an addition salt thereof with a pharmaceutically-acceptable base.

3. A compound according to claim 1 which is selected from N-(4,6-dimethylpyridin-2-yl)-(6-hydroxy-2,5,7,8-tetramethylchroman-2-yl)carboxamide, an isomer thereof, and an addition salt thereof with a pharmaceutically-acceptable base.

4. A compound according to claim 1 which is selected from N-ethyl-N-(4,6-dimethylpyridin-2-yl)-(6-hydroxy-2,5,7,8-tetramethylchroman-2-yl)carboxamide, an isomer thereof, and an addition salt thereof with a pharmaceutically-acceptable base.

5. A compound according to claim 1 which is selected from N-methyl-N-(4,6-dimethylpyridin-2-yl)-(6-hydroxy-2,5,7,8-tetramethylchroman-2-yl)carboxamide, an isomer thereof, and an addition salt thereof with a pharmaceutically-acceptable base.

6. A compound according to claim 1 which is selected from N-(4,6-dimethylpyridin-2-yl)-(6-acetoxy-2,5,7,8-tetramethylchroman-2-yl)carboxamide, an isomer thereof, and an addition salt thereof with a pharmaceutically-acceptable base.

7. A compound according to claim 1 which is selected from N-ethyl-N-(4,6-dimethylpyridin-2-yl)-(6-acetoxy-2,5,7,8-tetramethylchroman-2-yl)carboxamide, an isomer thereof, and an addition salt thereof with a pharmaceutically-acceptable base.

8. A compound according to claim 1 which is selected from N-methyl-N-(4,6-dimethylpyridin-2-yl)-(6-methoxy-2,5,7,8-tetramethylchroman-2-yl)carboxamide, an isomer thereof, and an addition salt thereof with a pharmaceutically-acceptable base.

9. A pharmaceutical composition, useful in treating or in preventing a disorder resulting from or associated with phenomena of peroxidation and disturbance of the synthesis of eicosanoids, selected from atheroma, ischemia, and inflammation, comprising as active principle an effective amount of a compound as claimed in claim 1, in combination with a pharmaceutically-acceptable carrier or diluent.

* * * * *

UNITED STATES PATENT AND TRADEMARK OFFICE
CERTIFICATE OF CORRECTION

PATENT NO. : 5,290,797

DATED : March 1, 1994

INVENTOR(S) : Guillaume Le Baut

It is certified that error appears in the above-indentified patent and that said Letters Patent is hereby corrected as shown below:

Col. 2, line 65; insert a hyphen between "$R_2$" and "Hal".
Col. 3, Formula $I_c$; this formula should be -- 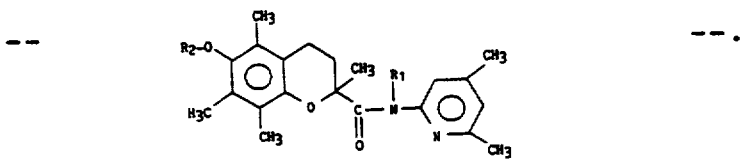 --.

Col. 3, line 13; "formula I an which" should read -- formula I in which --.
Col. 5, line 34; "Example 2 N" should read -- Example 2 N- --.
Col. 5, line 36; insert a hyphen after "thylchroman".
Col. 5, line 51; insert a hyphen both before and after the "2".
Col. 5, line 52; insert a hyphen both before and after the second "2".
Col. 6, line 42; insert a colon after "Examples 7 to 9".
Col. 6, line 60; "Example 9:" should be centered, everything following it should be moved down to the next line, and insert a hyphen after the "2".

UNITED STATES PATENT AND TRADEMARK OFFICE
CERTIFICATE OF CORRECTION

PATENT NO. : 5,290,797
DATED : March 1, 1994
INVENTOR(S) : Guillaume Le Baut

It is certified that error appears in the above-indentified patent and that said Letters Patent is hereby corrected as shown below:

Col. 7, line 1; "Example 10:" should be centered, everything following it should be moved down to the next line, and insert a hyphen after "propoxy".
Col. 7, line 52; insert a hyphen after the "8".
Col. 7, line 59; insert a hyphen after "(4,6".
Col. 7, line 66; delete the "o" before "filter".
Col. 8, line 17; insert a hyphen after the "2".
Col. 8, line 33; insert a hyphen after the "8".
Col. 8, line 36; insert a hyphen before "yl".
Col. 8, line 60; ".OH " should read -- ·OH --.
Col. 10, line 57; delete "N-methyl-".

Signed and Sealed this

Twenty-fifth Day of October, 1994

Attest:

BRUCE LEHMAN

Attesting Officer        Commissioner of Patents and Trademarks